United States Patent
Baumann et al.

(10) Patent No.: US 7,851,656 B2
(45) Date of Patent: Dec. 14, 2010

(54) METHOD FOR PRODUCING ORGANIC PHOSPHOROUS COMPOUNDS CONTAINING HALOGENS

(75) Inventors: Robert Baumann, Mannheim (DE); Tobias Aechtner, Mannheim (DE); Wolfgang Siegel, Limburgerhof (DE); Hermann Luyken, Ludwigshafen (DE); Peter Pfab, Neustadt (DE); Jens Scheidel, Hirschberg (DE); Andreas Leitner, Ludwigshafen (DE); Andreas Glass, Lambsheim (DE)

(73) Assignee: BASF SE (DE)

( * ) Notice: Subject to any disclaimer, the term of this patent is extended or adjusted under 35 U.S.C. 154(b) by 35 days.

(21) Appl. No.: 12/373,336

(22) PCT Filed: Jul. 3, 2007

(86) PCT No.: PCT/EP2007/056685

§ 371 (c)(1),
(2), (4) Date: Jan. 12, 2009

(87) PCT Pub. No.: WO2008/006735

PCT Pub. Date: Jan. 17, 2008

(65) Prior Publication Data

US 2009/0281356 A1 Nov. 12, 2009

(30) Foreign Application Priority Data

Jul. 12, 2006 (EP) .................................. 06117037

(51) Int. Cl.
*C07F 9/02* (2006.01)
(52) U.S. Cl. ........................................ 568/14
(58) Field of Classification Search ........................ None
See application file for complete search history.

(56) References Cited

U.S. PATENT DOCUMENTS 4,661,615 A * 4/1987 Boyle et al. ................. 558/363
2004/0106815 A1 * 6/2004 Ritter ......................... 558/128

2005/0020857 A1  1/2005 Volland et al.

FOREIGN PATENT DOCUMENTS

| WO | WO 01/32666 | * | 5/2001 |
| WO | WO-01/32666 A1 | | 5/2001 |
| WO | WO-03/062251 A1 | | 7/2003 |

OTHER PUBLICATIONS

Pastor et al., {Sterically hindered phosphonites, Phosphorus and Sulfur and the Related Elements,(1985), 22(2), 169-176}.*
Herberich, G.E., et al., "1,1'-Bis(methylphenylphosphanyl)ferrocene: synthesis and complexes with the tetracarbonylchromium fragment," Chem. Ber., 1995, vol. 128, pp. 689-693.
Pastor, S.D., et al., "Sterically hindered phophonites," Phosphorus and Sulfur, 1985, vol. 22, pp. 169-176.

* cited by examiner

*Primary Examiner*—Daniel M Sullivan
*Assistant Examiner*—Chukwuma O Nwaonicha
(74) *Attorney, Agent, or Firm*—Connolly Bove Lodge & Hutz LLP

(57) ABSTRACT

Method of producing compounds of the general formula $$XPR^2(OR^1) \qquad \text{Ia}$$

where X is chlorine, bromine or iodine and $R^1$ is an organic radical, by reacting compounds of the general formula $$X_2PR^2 \qquad \text{II,}$$

in which X has the meaning given above and $R^2$ is an organic radical, with compounds of the general formula $$R^1OH \qquad \text{III,}$$

in which $R^1$ has the meaning given above, to give a mixture IV, in that
a) the postreaction is carried out at a temperature of from 50 to 240° C. and a pressure of from 0.001 to 0.9 bar,
b) from the mixture IV the compounds Ia are separated off from the compounds $$PR^2(OR^1)_2 \qquad \text{Ib}$$

and, if appropriate, the compounds II and
c) compounds Ib and, if appropriate, unreacted compounds II are returned to the synthesis stage.

17 Claims, No Drawings

METHOD FOR PRODUCING ORGANIC PHOSPHOROUS COMPOUNDS CONTAINING HALOGENS

CROSS-REFERENCE TO RELATED APPLICATIONS

Related Applications

This application is a national stage application (under 35 U.S.C. §371) of PCT/EP2007/056685, filed Jul. 3, 2007, which claims benefit of European application 06117037.9, filed Jul. 12, 2006.

BACKGROUND OF THE INVENTION

The present invention relates to an improved method of producing organic phosphorus compounds comprising halogens of the formula $$XPR^2(OR^1) \qquad \text{Ia,}$$

in which X is halogens and $R^1$ and $R^2$ are organic radicals.

It is known from WO 01/32 666 A 1 (DE 199 53 048) that organic phosphorus compounds comprising halogens of the formulae $$X_{(1-a)}R^2{}_aP(OR^1)_2 \qquad \text{I or}$$

$$X_{(2-a)}R^2{}_aP(OR^1) \qquad \text{II,}$$

in which X may be a halogen, R1 and R2 may be organic radicals and a may be the values 0 or 1, can be produced by reacting a compound of the formula $$X_{(3-a)}R^2{}_aP \qquad \text{III with a compound of the formula}$$

$$R^1OH \qquad \text{IV}$$

at 10 to 200° C. and atmospheric pressure. This gives a mixture V which comprises the compounds I and II. The compounds I and II are separated from one another. If compound I is the target product, compound II is returned to the synthesis step. If compound II is the target product, compound I is returned.

The disadvantage when producing compounds II where a=1 from compounds III where a=1 is that the reactant $R^1OH$ is not completely reacted when working atmospheric pressure. If the reaction products are worked up by distillation in order to isolate the target products, then the unreacted halogen-comprising organic phosphorus compounds II (a=1) react with the compounds $R^1OH$ to form hydrogen chloride and increase the amount of product which has to be returned. Furthermore, the target product II has to be purified from hydrogen chloride.

BRIEF SUMMARY OF THE INVENTION

The object of the present invention was to avoid these disadvantages. The aim here was to achieve as high a yield of the target product Ia as possible, to minimize the amount of product Ib to be returned, and to simplify the work-up of the reaction product and the return of the products Ib.

These objects are achieved in a method of producing compounds of the general formulae $$XPR^2(OR^1) \qquad \text{Ia}$$

where X is chlorine, bromine or iodine and $R^1$ is an organic radical, by reacting compounds of the general formula $$X_2PR^2 \qquad \text{II,}$$

in which X has the meaning given above and $R^2$ is an organic radical, with compounds of the general formula $$R^1OH \qquad \text{III,}$$

in which $R^1$ has the meaning given above, to give a mixture IV, wherein
a) the postreaction is carried out at a temperature of from 50 to 240° C. and a pressure of from 0.001 to 0.9 bar,
b) from the mixture IV the compounds Ia are separated off from the compounds $$PR^2(OR^1)_2 \qquad \text{Ib}$$

and, if appropriate, the compounds II and
c) compounds Ib and, if appropriate, unreacted compounds II are returned to the synthesis stage.

DETAILED DESCRIPTION OF THE INVENTION

The reaction can be carried out discontinuously or continuously, preferably discontinuously as a batch process.

In the case of a discontinuous batch procedure, compound III can be initially introduced and compound II added. However, it is preferred to initially introduce compound II and to add compound III. The rate of the addition of III depends on how quickly the hydrogen chloride which forms can be removed.

The feed materials II and III can be reacted at temperatures of from 50 to 240° C., preferably 80 to 210° C., particularly preferably 120 to 200° C. and ambient pressure. The bringing together of the reactants generally lasts 0.5 to 10 hours, preferably 1 to 5 hours.

The molar ratio of starting material II to starting material III is generally 1.5 to 1, preferably 1.3 to 1, particularly preferably 1 to 1.

Postreaction

After the reactants have been brought together in a discontinuous procedure, the postreaction follows. The reaction is completed in this time. This takes place at temperatures of from 50 to 240° C., preferably 80 to 210° C., particularly preferably 120 to 200° C. and a pressure of from 0.001 to 0.9 bar, preferably 0.003 to 0.5 bar, particularly preferably 0.005 to 0.4 bar.

The reaction is carried out such that during the entire postreaction time, preferably during some of the postreaction time, temperatures above the boiling points of the two starting materials II and III and below the boiling points of the reaction products Ia and Ib are used. Preference here is given to working under reflux of starting materials II and III.

In a particularly preferred embodiment of the method, the reaction pressure during the postreaction time is reduced step for step in order to keep the boiling of the starting materials II and III going.

This procedure can achieve a conversion of starting material III of >97%, preferably >98%, particularly preferably >99%. This facilitates distillative work-up of the reaction mixture since it then consists only of components Ia, Ib and, if appropriate, furthermore significant HCl formation no longer takes place during distillative work-up.

The reaction mixture is afterstirred for 0.5 to 15 hours, preferably one to 12 hours, particularly preferably 1.5 to 10 hours.

The hydrogen halide which forms during the reaction, in gaseous form under the reaction conditions, can advantageously be separated off in gaseous form and neutralized, or can be passed as feed material to chemical processes known per se.

Work-up of the Reaction Product

From the resulting reaction product, firstly unreacted compound II, then the target product Ia are distilled off during distillative work-up. Compound Ib is obtained as bottom product.

Return of Compound Ib

In the case of discontinuous batch procedure in which the synthesis can be carried out for example, in a reaction vessel with attached column, compound Ib remains as high-boiling component in the reaction vessel. Compound II or mixtures of compound II and Ia, also compound III are topped up. The reaction for producing compound Ia with the return of reaction products can be carried out under the same reaction conditions as starting from the compounds II and III as starting materials.

Since the compounds Ib can be returned and additional by-products only form in small amounts, a high yield of the target products Ia can be achieved.

Suitable organic radicals R1 and R2 in the formulae I to III are, independently of one another, advantageously alkyl radicals and, in particular, aromatic radicals.

Suitable alkyl radicals are $C_1$- to $C_{18}$-alkyl, preferably $C_1$- to $C_{12}$-alkyl, particularly preferably $C_1$- to $C_8$-alkyl, such as methyl, ethyl, n-propyl, isopropyl, n-butyl, isobutyl, sec-butyl, tert-butyl, n-pentyl, and isomeric pentyls, n-hexyl, and isomeric hexyls, or $C_3$- to $C_{12}$-cycloalkyl, preferably $C_4$- to $C_8$-cycloalkyl, particularly preferably $C_5$- to $C_7$-cycloalkyl, such as cyclopentyl or cyclohexyl, where the cyclic alkyl radicals can carry linear or further cyclic alkyl radicals or aromatic radicals and the alkyl radicals can carry cyclic alkyl radicals or aromatic radicals as substituents.

These alkyl radicals can carry further functional groups, such as $C_1$- to $C_8$-alkoxy, 1- or 2-naphthyloxy, phenyloxy, diamino, mercapto or halogen, such as chlorine, bromine or iodine. Preferably, the alkyl radicals carry no functional groups.

In the alkyl radicals with at least 2 carbon atoms, preferably with at least 3 carbon atoms, one carbon atom can be substituted by another atom such as oxygen, nitrogen or sulfur. In the alkyl radicals with at least 4 carbon atoms, preferably with at least 5 carbon atoms, one or two carbon atoms can be substituted by one or two identical or different atoms such as oxygen, nitrogen or sulfur. Preferably, the alkyl radicals are not substituted.

Suitable aromatic radicals are heterocycles, preferably homocycles, such as 1- and 2-naphthyl, preferably phenyl.

These aromatic radicals can carry further functional groups, such as $C_1$- to $C_{18}$-alkoxy, 1- or 2-naphthyloxy, phenyloxy, diamino, mercapto or halogens, such as chlorine, bromine or iodine.

These aromatic radicals can carry alkyl radicals, Suitable alkyl radicals are $C_1$- to $C_{18}$-alkyl, preferably $C_1$- to $C_{12}$-alkyl, particularly preferably $C_1$- to $C_8$-alkyl, such as methyl, ethyl, n-propyl, isopropyl, n-butyl, isobutyl, sec-butyl, tert-butyl, n-pentyl, and isomeric pentyls, n-hexyl, and isomeric hexyls, or $C_3$- to $C_{12}$-cycloalkyl, preferably $C_4$- to $C_8$-cycloalkyl, particularly preferably $C_5$- to $C_7$-cycloalkyl, such as cyclopentyl or cyclohexyl, where the cyclic alkyl radicals can carry linear or further cyclic alkyl radicals or aromatic radicals and the alkyl radicals can carry cyclic alkyl radicals or aromatic radicals as substituents.

These alkyl radicals can carry further functional groups, such as $C_1$- to $C_8$-alkoxy, 1- or 2-naphthyloxy, phenyloxy, diamino, mercapto or halogens, such as chlorine, bromine or iodine. Preferably, the aromatic radicals carry no functional groups.

In the alkyl radicals with at least 2 carbon atoms, preferably with at least 3 carbon atoms, one carbon atom can be substituted by another atom such as oxygen, nitrogen or sulfur. In the alkyl radicals with at least 4 carbon atoms, preferably with at least 5 carbon atoms, one or two carbon atoms can be substituted by one or two identical or different atoms such as oxygen, nitrogen or sulfur. Preferably, the alkyl radicals are not substituted.

These aromatic radicals can carry aromatic substituents.

Suitable aromatic substituents are heterocycles, preferably homocycles, such as 1- or 2-naphthyl, preferably phenyl.

These aromatic substituents can carry further functional groups, such as $C_1$- to $C_8$-alkoxy, 1- or 2-naphthyloxy, phenyloxy, diamino, mercapto or halogens, such as chlorine, bromine or iodine. Preferably, the aromatic radicals carry no functional groups.

These aromatic substituents can carry alkyl radicals, Suitable alkyl radicals are $C_1$- to $C_{18}$-alkyl, preferably $C_1$- to $C_{12}$-alkyl, particularly preferably $C_1$- to $C_8$-alkyl, such as methyl, ethyl, n-propyl, isopropyl, n-butyl, isobutyl, sec-butyl, tert-butyl, n-pentyl, and isomeric pentyls, n-hexyl, and isomeric hexyls, or $C_3$- to $C_{12}$-cycloalkyl, preferably $C_4$- to $C_8$-cycloalkyl, particularly preferably $C_5$- to $C_7$-cycloalkyl, such as cyclopentyl or cyclohexyl, where the cyclic alkyl radicals can carry linear or further cyclic alkyl radicals or aromatic radicals and the alkyl radicals can carry cyclic alkyl radicals or aromatic radicals as substituents.

These alkyl radicals can carry further functional groups, such as $C_1$- to $C_8$-alkoxy, 1- or 2-naphthyloxy, phenyloxy, diamino, mercapto or halogens, such as chlorine, bromine or iodine. Preferably, the aromatic radicals carry no functional groups.

In the alkyl radicals with at least 2 carbon atoms, preferably with at least 3 carbon atoms, one carbon atom can be substituted by another atom such as oxygen, nitrogen or sulfur. In the alkyl radicals with at least 4 carbon atoms, preferably with at least 5 carbon atoms, one or two carbon atoms can be substituted by one or two identical or different atoms such as oxygen, nitrogen or sulfur. Preferably, the alkyl radicals are not substituted.

If the aromatic radical used is the phenyl radical, then the phenyl radical can carry an alkyl radical or aromatic substituents in the o-, m- or p-position.

Compound II can be used as an individual compound or as a mixture of different compounds, preferably as an individual compound. It is also possible to use mixtures of different identically or differently halogen-substituted compounds of type II.

Particularly preferred compounds II are phenyldichlorophosphine, ethyldichlorophosphine, methyldichlorophosphine, p-tolyidichlorophosphine, o-tolyidichlorophosphine, m-tolyldichlorophosphine, 1-naphthyldichlorophosphine, 2-naphthyldichlorophosphine, o-anisyldichlorophosphine.

Compound III can be used as an individual compound or as a mixture of different compounds, preferably as an individual compound.

Particularly preferred compounds III are phenol, ortho-cresol, meta-cresol, para-cresol, ortho-ethylphenol, meta-ethylphenol, para-ethylphenol, ortho-n-propylphenol, meta-n-propylphenol, para-n-propylphenol, ortho-isopropylphenol, meta-isopropylphenol, para-isopropylphenol, ortho-n-butylphenol, meta-n-butylphenol, para-n-butylphenol, ortho-isobutylphenol, meta-isobutylphenol, para-isobutylphenol, ortho-sec-butylphenol, meta-sec-butylphenol, para-sec-butylphenol, ortho-tert-butylphenol, meta-tert-butylphenol, para-tert-butylphenol.

The phosphorus compounds of type I obtainable by the method according to the invention are suitable, for example, for the synthesis of flame retardants, active ingredients and homogeneous catalysts.

EXAMPLES

Example 1

Synthesis of chloro(2-tert-butylphenoxy)phenylphosphine (CPP) from dichlorophenylphosphine (DCPP) and 2-tert-butylphenol

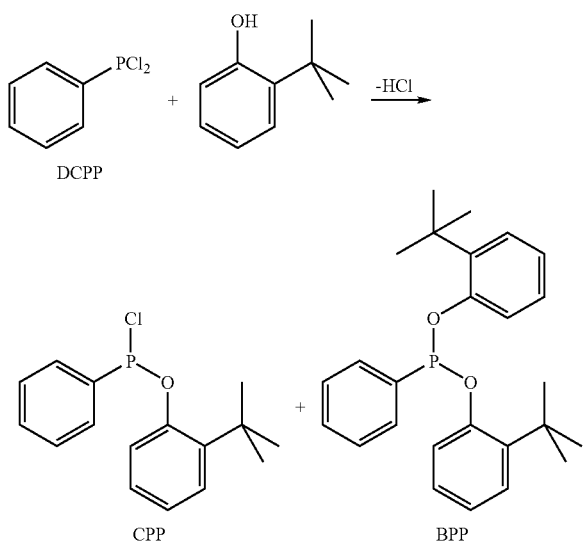

The reaction was carried out in a 500 ml four-necked flask with magnetic stirrer, dropping funnel, condenser, bubble counter and attached packed column (5 theoretical trays) under argon.

179 g of dichlorophenylphosphine (1.0 mol), heated to 150° C., were initially introduced into the flask. Under stirring at atmospheric pressure, 150 g of 2-tert-butylphenol (1.0 mol) were added dropwise at this temperature over the course of two hours. The hydrogen chloride which formed was passed over a wash tower with 15% strength aqueous sodium hydroxide solution. The mixture was then afterstirred for one hour at 150° C. and a sample S1 was taken from the reactor.

Then, at 150° C., a vacuum was applied. Firstly 50 mbar, during which reflux started in the reaction flask. As reflux subsided, the pressure was taken back to 30 mbar. Overall, the reaction mixture was stirred for three hours at 150° C. under reduced pressure. The sample S2 was taken from the flask.

Gas chromatograms of samples S1 and S2 revealed that in sample S1 8.3 area-% of 2-tert-butylphenol were still present, and in sample S2 only less than 1% of 2-tert-butylphenol was still present.

Quantitative analysis of the reaction product (Sample S2) using $^{31}$P NMR revealed that the yield of chloro(2-tert-butylphenoxy)phenylphosphine (CPP) was 69.4% (based on DCPP used). The yield of diarylated product BPP was 14.6% and of unreacted dichlorophenylphosphine 14.9% (in each case based on DCPP used).

The HCl-free reaction mixture was worked up by distillation. CPP and DCPP were distilled off stepwise under reduced pressure via the attached column. As fore-runnings, 22 g of DCPP (12%, based on DCPP used) were obtained at 184° C./14 mbar. As intermediate runnings, 5 g of a mixture of DCPP and CPP were isolated at 184-195° C./5 mbar. The main runnings consisted of 195 g of CPP (67%, based on DCPP used), which passed over at 195° C./2 mbar. 57 g of high-boiling BPP remained in the flask.

Comparative Example

The reaction of DCPP with 2-tert-butylphenol was carried out in an identical way to Example 1 as far as its complete addition to the reaction flask. The mixture was then stirred at ambient pressure without reflux for four hours at 150° C. The mixture was then cooled to room temperature. The gas chromatogram of a sample of the reaction product revealed that it still comprised 7.5 area-% of 2-tert-butylphenol.

Quantitative analysis of the reaction product with the help of $^{31}$P NMR revealed that the yield of chloro(2-tert-butylphenoxy)phenylphosphine (CPP) was 65% (based on DCPP used). The yield of diarylated product was 6% and of unreacted dichlorophenylphosphine 21% (in each case based on DCPP used).

The invention claimed is:

1. A method of producing compounds of the formula $$XPR^2(OR^1) \qquad \text{Ia}$$

where X is chlorine, bromine or iodine and $R^1$ is an organic radical which comprises reacting a compound of the a formula $$X_2PR^2 \qquad \text{II,}$$

in which X has the meaning given above and $R^2$ is an organic radical, with a compound of the formula $$R^1OH \qquad \text{III,}$$

in which $R^1$ has the meaning given above, to give a mixture IV, wherein
 a) the postreaction is carried out at a temperature of from 50 to 240° C. and a pressure of from 0.001 to 0.9 bar,
 b) from the mixture IV the compound Ia is separated off from the compound $$PR^2(OR^1)_2 \qquad \text{Ib}$$

and, optionally the compounds II and
 c) compounds Ib and optionally unreacted compounds II are returned to the synthesis stage.

2. The method according to claim 1, wherein the postreaction is carried out above the boiling points of compounds II and III under reflux of some of the reaction mixture.

3. The method according to claim 1, wherein the postreaction is carried out below the boiling points of compounds Ia and Ib under reflux of some of the reaction mixture.

4. The method according to claim 1, wherein the organic radicals $R^1$ and $R^2$ used are, independently of one another, $C_1$- to $C_{18}$-alkyl radicals or aromatic radicals.

5. The method according to claim 4, wherein $R^1$ and $R^2$ are phenyl or naphthyl radicals which may be substituted in the o-, m- and/or p-position by alkyl or alkoxy groups.

6. The method according to claim 1, wherein $R^1$ is ortho-tert-butylphenyl.

7. The method according to claim 1, wherein X is chlorine.

8. The method according to claim 1, wherein $R^2$ is phenyl.

9. The method according to claim 1, wherein the reaction is carried out at a temperature of from 120 to 200° C.

10. The method according to claim 1, wherein the reaction is carried out at a pressure of from 0.005 to 0.4 bar.

11. The method according to claim 6, wherein X is chlorine.

12. The method according to claim 11, wherein $R^2$ is phenyl.

13. The method according to claim 12, wherein the reaction is carried out at a temperature of from 120 to 200° C.

14. The method according to claim 13, wherein the reaction is carried out at a pressure of from 0.005 to 0.4 bar.

15. The method according to claim 1, wherein the reaction is carried out continuously.

16. The method according to claim 1, wherein the reaction is carried out as a batch process.

17. The method according to claim 1, wherein the reaction is carried out at a temperature of from 80 to 210° C.

* * * * *